United States Patent

Chan et al.

Patent Number: 5,228,461
Date of Patent: Jul. 20, 1993

[54] SMOKING COMPOSITIONS CONTAINING A VANILLIN-RELEASE ADDITIVE

[75] Inventors: W. Geoffrey Chan, Richmond; Harvey J. Grubbs, Mechanicsville; Yoram Houminer, Richmond; Kenneth F. Podraza, Richmond; Edward B. Sanders, Richmond, all of Va.

[73] Assignees: Philip Morris Incorporated, New York, N.Y.; Philip Morris Products Inc., Richmond, Va.

[21] Appl. No.: 946,519

[22] Filed: Sep. 16, 1992

Related U.S. Application Data

[62] Division of Ser. No. 688,436, Apr. 22, 1991, Pat. No. 5,172,704.

[51] Int. Cl.$^5$ .............................................. A24B 15/30
[52] U.S. Cl. .................................... 131/276; 131/274; 568/425; 558/271
[58] Field of Search .................. 131/274, 276, 278; 568/425, 442; 558/271

[56] References Cited

U.S. PATENT DOCUMENTS

| | | | |
|---|---|---|---|
| 4,120,830 | 10/1978 | Renold et al. | 252/522 |
| 4,141,906 | 2/1979 | Teng | 260/340.5 H |
| 4,509,537 | 4/1985 | Houminer et al. | 558/271 |
| 4,804,002 | 2/1989 | Herron | 131/365 |
| 5,120,368 | 6/1992 | Houminer et al. | 131/278 |
| 5,129,954 | 7/1992 | Chan et al. | 131/276 |

Primary Examiner—Randall L. Green
Assistant Examiner—Paul Prebilic
Attorney, Agent, or Firm—James E. Schardt

[57] ABSTRACT

This invention provides smoking compositions which contain a novel vanillin flavorant-release additive.

A cigarette smoking product comprising (1) a combustible filler selected from natural tobacco, reconstituted tobacco and tobacco substitutes, and (2) a paper wrapper which has incorporated therein a flavorant-release additive corresponding to the formula:

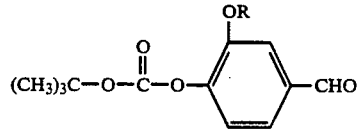

where R is methyl or ethyl.

12 Claims, No Drawings

SMOKING COMPOSITIONS CONTAINING A VANILLIN-RELEASE ADDITIVE

This application is a division of application Ser. No. 07/688,436, filed Apr. 22, 1991, now U.S. Pat. No. 5,172,704.

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,772,516; 3,750,674; 3,879,425; 3,881,025; 3,884,247; 3,890,981; 3,914,451; 3,915,175; 3,920,027; 3,924,644; 3,937,228; 3,943,943; 3,586,387; 3,379,754; and the like.

J. C. Leffingwell et al. "Tobacco Flavoring For Smoking Products" (R. J. Reynolds publication, 1972) recites a listing of desirable flavorants for smoking compositions, which includes phenols, terpenols and lactones such as guaiacol, 1-undecanol and 5-dodecalactone.

The high degree of volatility and ease of evaporation or sublimation of flavorant additives in tobacco products have presented problems in the manufacturing operations, and have resulted in a decreased shelf-life of the products due to losses of flavorant by evaporation on storage.

Recent developments have involved incorporated a low volatility organic additive to a smoking composition, which under smoking conditions is pyrolyzed into one or more fragments that function to improve the taste and character of mainstream tobacco smoke, and in some cases a consequential improvement of sidestream smoke aroma.

U.S. Pat. No. 3,312,226 describes smoking tobacco compositions which contain an ester additive such as 1-methyl linalool carbonate. Under smoking conditions pyrolysis of the carbonate ester releases menthol which flavors the mainstream smoke.

U.S. Pat. No. 3,332,428 and U.S. Pat. No. 3,419,543 describe smoking tobacco compositions which contain a menthol carbonate ester of a glycol or saccharide, which under smoking conditions decomposes to release free menthol into the mainstream smoke.

U.S. Pat. No. 3,499,452 discloses similar smoking tobacco compositions in which a carbonate ester additive releases flavorant volatiles other than menthol.

U.S. Pat. Nos. 4,119,106; 4,171,702; 4,177,339; and 4,212,310 describe other oligomeric and polymeric carbonate ester derivatives which as constituents of smoking compositions are stable and non-volatile under storage conditions, and are adapted to release pyrolysis products under smoking conditions that improve the taste and aroma of the smoke.

U.S. Pat. Nos. 4,036,237; 4,141,906; and 4,178,458 describe β-hydroxyesters which as additives in smoking compositions pyrolyze into volatile aldehyde and ester flavorants under smoking conditions.

U.S. Pat. Nos. 4,473,085 and 4,607,118 describe β-hydroxyesters which as additives in smoking compositions pyrolyze into volatile ketone and ester flavorants under smoking conditions.

Of particular interest with respect to the present invention is the proposed utilization of an organic additive to a cigarette paper wrapper to enhance sidestream smoke aroma under smoking conditions. U.S. Pat. No. 4,804,002 describes a tobacco product wrapper containing a flavorant additive comprising a glycoside of a carbohydrate and phenolic compound. Under cigarette smoking conditions a flavorant additive such as ethylvanillyl D-glucoside yields ethylvanillin and levoglucosan as pyrolysis products.

The subject matter of this application is similar to that disclosed in U.S. Pat. No. 5,129,954.

There is a continuing research effort to develop low delivery smoking compositions which generate mainstream smoke with enhanced taste and sidestream smoke with a pleasant aroma under smoking conditions.

Accordingly, it is an object of this invention to provide smoking compositions having incorporated therein a flavorant-release component which is characterized by lack of mobility and/or volatility at ambient temperature.

It is another object of this invention to provide cigarette smoking products having a paper wrapper which has incorporated therein a flavorant-release additive which under normal smoking conditions imparts improved aroma to sidestream smoke.

It is a further object of this invention to provide novel substituted benzaldehyde and β-hydroxyester compounds which are adapted to be incorporated into cigarette filler and/or paper wrapper components, and which under normal smoking conditions release volatile ester and vanillin flavorants into cigarette smoke.

Other objects and advantages of the present invention shall become apparent from the following description and examples.

DESCRIPTION OF THE INVENTION

One or more objects of the present invention are accomplished by the providing of a smoking composition comprising an admixture of (1) combustible filler selected from natural tobacco, reconstituted tobacco and tobacco substitutes, and (2) between about 0.0001–5 weight percent, based on the total weigh of filler, of a flavorant-release additive corresponding to the formula:

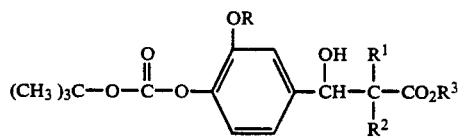

where R is methyl or ethyl; $R^1$ is hydrogen or a $C_1$–$C_4$ alkyl substituent; $R^2$ is hydrogen or a $C_1$–$C_4$ alkyl or $C_6$–$C_{10}$ aromatic substituent; and $R^3$ is a $C_1$–$C_4$ alkyl or $C_6$–$C_{10}$ aromatic substituent.

In another embodiment this invention provides a smoking composition comprising an admixture of (1) combustible filler selected from natural tobacco, reconstituted tobacco and tobacco substitutes, and (2) between about 0.0001–5 weight percent, based on the total weight of filler, of a flavorant-release additive corresponding to the formula:

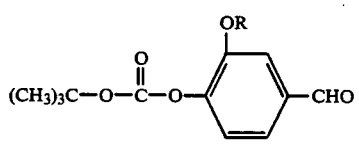

where R is methyl or ethyl.

In another embodiment this invention provides a cigarette smoking product comprising (1) a combustible filler selected from natural tobacco, reconstituted tobacco and tobacco substitutes, and (2) a paper wrapper which has incorporated therein a flavorant-release additive corresponding to the formula:

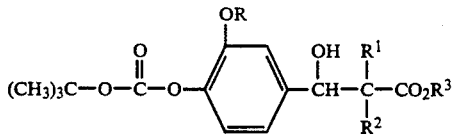

where R is methyl or ethyl; $R^1$ is hydrogen or a $C_1$–$C_4$ alkyl substituent; $R^2$ is hydrogen or a $C_1$–$C_4$ alkyl or $C_6$–$C_{10}$ aromatic substituent; and $R^3$ is a $C_1$–$C_4$ alkyl or $C_6$–$C_{10}$ aromatic substituent.

In another embodiment this invention provides a cigarette smoking product comprising (1) a combustible filler selected from natural tobacco, reconstituted tobacco and tobacco substitutes, and (2) a paper wrapper which has incorporated therein a flavorant-release additive corresponding to the formula:

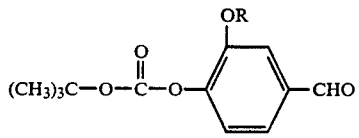

where R is methyl or ethyl.

Illustrative of $C_1$–$C_4$ alkyl substituents in the above represented flavorant-release additive formula I are methyl, ethyl, propyl, 2-propyl, butyl, 2-butyl and isobutyl groups.

Illustrative of $C_6$–$C_{10}$ aromatic substituents are phenyl, tolyl, xylyl, benzyl, phenylethyl, methoxyphenyl, and the like.

A cigarette smoking product in accordance with the present invention typically contains between about 0.01–5 weight percent of flavorant-release additive in the paper wrapper, based on the weight of combustible filler.

In a further embodiment an invention cigarette product contains between about 0.01–5 weight percent of flavorant-release additive in the paper wrapper, and contains between about 0.0001–5 weight percent of flavorant-release additive in the combustible filler, based on the weight of filler.

A present invention flavorant-release additive in accordance with formula I which is incorporated in smoking compositions as described above is a low volatility compound which under normal smoking conditions pyrolyzes into volatile constituents which enhance the flavor and aroma of low delivery cigarette smoke:

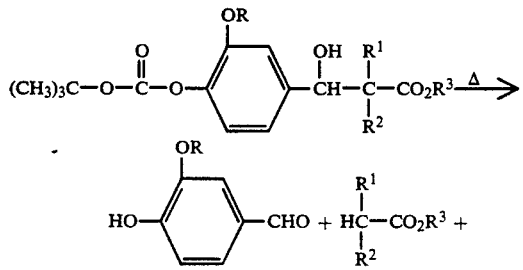

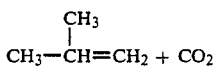

where R, $R^1$, $R^2$ and $R^3$ are as previously defined.

An important feature of an invention smoking composition having a formula I additive is the release of two flavorants under smoking conditions, one of which is an ester and the other is vanillin or ethylvanillin.

Both the ester and vanillin volatiles which are released have exceptional organoleptic properties. Each of the compounds contributes a pleasant flavor and aroma to cigarette smoke.

In a similar manner, a present invention flavorant-release additive in accordance with formula II is a low volatility compound which pyrolyzes to release vanillin and other volatiles:

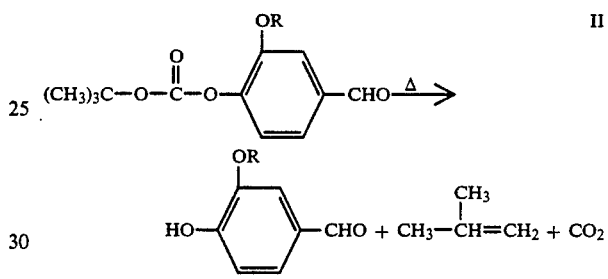

where R is methyl or ethyl. The pyrolysis of a formula II compound proceeds smoothly and quantitatively at a temperature as low as 175° C.

An important advantage of a present invention formula I or II flavorant-release compound is an excellent stability property when utilized as a cigarette paper additive and the paper is exposed to variable conditions of light and moisture. Cigarette paper treated with a present invention flavorant-release additive does not discolor under light and moisture exposure conditions due to decomposition of the additive.

Preparation of Flavorant-release Compounds

One procedure for the preparation of the invention flavorant-release compounds is by (1) the reaction of vanillin or ethylvanillin with di-t-butyl dicarbonate to provide a formula II type compound, and (2) the subsequent reaction of the formula II compound with a metallated alkanoate derivative to provide a formula I type compound:

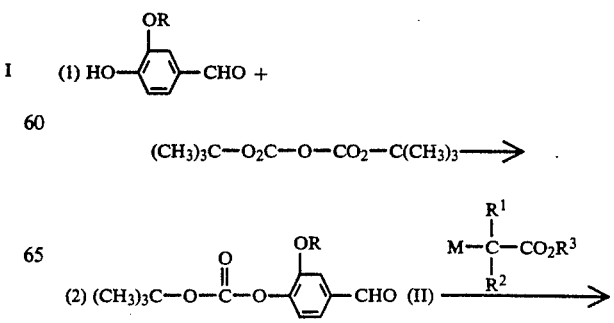

-continued

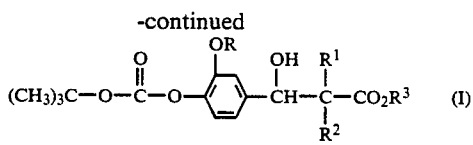

where M in the metallated alkanoate is a monovalent metal atom such as lithium, sodium or potassium.

The metallated alkanoate is formed in the presence of a strong base such as lithium diisopropylamide or alkali metal hydride.

In a typical procedure the base is added to the alkanoate in an inert solvent medium such as tetrahydrofuran or diethyl ether, maintained at a temperature between about −80° C. and 50° C. under and inert atmosphere.

Preparation Of Tobacco Compositions

In a further embodiment the present invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a flavorant-release additive corresponding to formula I or formula II as defined above.

The invention flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5–5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references cited therein, incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150° –750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

As previously described hereinabove, an invention flavorant-release additive also can be incorporated in the paper wrapper of cigarette products, for the purpose of enhancing the aroma of cigarette sidestream smoke under smoking conditions. The incorporation can be accomplished by coating the paper wrapper with a solvent solution of the flavorant-release additive, utilizing a size press or other conventional coating equipment. The flavorant-release additive also can be incorporated as a constituent of the composition used as a paper wrapper sidestream adhesive.

The following Examples are further illustrative of the present invention. The specific ingredients and processing parameters are presented as being typical, and various modifications can be derived in view of the foregoing disclosure within the scope of the invention.

EXAMPLE I

This Example illustrates the preparation of 4-t-butoxycarbonyloxy-3-methoxybenzaldehyde.

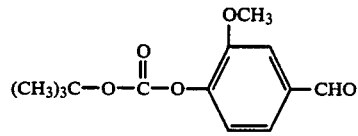

A 5-liter 3-necked round-bottomed flask equipped with a mechanical stirrer, an addition funnel and a thermometer was charged with vanillin (202 g, 1.33 moles) and ethyl acetate (1.5 L). The solution was heated to 42° C., powdered anhydrous sodium carbonate (140 g. 1.32 moles) was added in one portion, and the mixture was stirred vigorously. Di-t-butyl dicarbonate (309 g, 1.42 moles, 6.7% excess) was added via the addition funnel over a 30 minute period. After 2 hours at 42° C.–43° C., the solid phase was removed by filtration, and the solvent of the reaction medium was removed by rotary evaporation. The resulting crude solid product was recrystallized from ethyl acetate and hexane, and the recovered crystalline product was washed with 500 mL of 20% ethyl acetate in hexane. After drying in a vacuum desiccator, 280 g (85% yield) of product was obtained, mp 89.5° –90.5° C. NMR and IR spectra confirm the structure of the title compound.

A related compound is prepared by using ethylvanillin in place of vanillin as a reactant.

EXAMPLE II

This Example illustrates the preparation of ethyl 3-(4′-butoxycarbonyloxy-3′-methoxyphenyl)-3-hydroxy-2-phenylpropanoate.

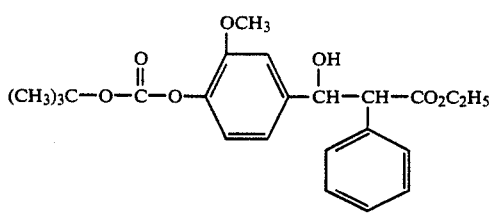

A 2liter 3-necked round-bottomed flask equipped with a mechanical stirrer, an addition funnel, a thermometer and a nitrogen source was charged with 250 mL (0.375 mole, 1.25 equivalent) of 1.5M lithium diisopropylamide in tetrahydrofuran/cyclohexane, and 250 mL of cyclohexane. The solution was cooled to −20° C., and ethyl phenylacetate (59 g, 0.36 mol, 1.2 equivalent) was added through the addition funnel while maintaining the temperature at −20° C. After addition was complete, the reaction mixture was maintained at −20° C. for 30 minutes.

4-t-Butoxycarbonyloxy-3-methoxybenzaldehyde (75.6 g, 0.3 mole) was dissolved in 250 mL of tetrahydrofuran, and the solution was added at a rapid rate to the reaction medium while maintaining the temperature at −20° C. Two hours after addition was complete, the reaction was cooled to about −40° C., and glacial acetic acid (54 g, 0.9 mole, 2.4 equivalent) was added rapidly to quench the reaction. The reaction medium temperature was increased to −20° C., water (250 mL) was added, and the mixture was stirred for 15 minutes as the temperature increased to above 0° C.

The aqueous layer was separated, and the organic layer was washed with water, and with saturated NaCl solution. The solution was dried over anhydrous magnesium sulfate and anhydrous sodium carbonate (50/50). HPLC of the solution indicated an absence of starting material.

The drying agent was filtered, and the solvent was removed by rotary evaporation to provide a light brownish oil. Hexane (500 mL) was added, and the mixture was stirred vigorously for 15 minutes. The white solid which formed was filtered and washed with 200 mL of hexane.

The solid was dissolved in 100 mL of ethyl acetate at 55° C., then hexane (400 mL) was added, and a solid precipitated when the solution was cooled to room temperature. The solid was recovered and washed with 10% ethyl acetate in hexane. After drying in a vacuum desiccator, 107 g (87% yield) of product was obtained.

HPLC analysis indicated that the product was composed of two diastereomers in a ratio of 35:65. NMR and IR Spectra confirm the structure of the title compound.

Related ester compounds are prepared by utilizing 4-t-butoxycarboxy-3-ethoxybenzaldehyde as a reactant, and/or methyl phenylacetate, butyl phenylacetate, methyl methoxyphenyl acetate, ethyl acetate, methyl propanoate or ethyl isobutyrate as a reactant in place of ethyl phenylacetate.

EXAMPLE III

This Example illustrates the thermolysis properties of invention vanillin-release compounds as compared to reference compounds.

The invention ethyl 3-(4'-butoxycarbonyloxy-3'-methoxyphenyl)-3-hydroxy-2-phenylpropanoate compound of Example II was compared with ethyl 3-hydroxy-3-(4'-hydroxy-3'-methoxyphenyl)-2-phenylpropanoate as a reference compound. Thermolysis was conducted by heating comparative samples in a quartz tube/furnace apparatus, and the pyrolysate was analyzed by GC/MS.

The invention t-butoxy-substituted compound of Example II pyrolyzed at 200° C. and 300° C. to give isobutene, carbon dioxide, vanillin and ethyl phenylacetate, and the reference compound pyrolyzed to vanillin and ethyl phenylacetate.

Thermal gravimetric analysis data indicated that the pyrolysis release temperature of both compounds was about 175° C.

In a further demonstration, the invention compound and the reference compound as ethanolic solutions respectively were applied to the paper wrapper of cigarettes (about 300 ppm), and the cigarettes were smoked and evaluated by an experienced smoking panel. Compared to untreated control cigarettes, all of the treated cigarettes exhibited a sweet, herbal-spicy, vanillin aroma in the sidestream smoke, without a significant change in mainstream smoke flavor.

A further comparative study of the invention compound of Example II and the reference compound was conducted. Cigarette paper samples containing the invention compound and the reference compound respectively were compared in the presence or absence of ultraviolet light, and in the presence or absence of moisture.

The test results indicated that the cigarette paper treated with the reference compound developed a yellow color due to a slight decomposition of the compound. Under the same test conditions, the cigarette paper treated with the invention compound of Example II did not develop a yellow color.

The 4-t-butoxycarbonyloxy-3-methoxybenzaldehyde of Example I was subjected to similar studies as described above. The Example I compound underwent smooth pyrolysis at 200° C. and 300° C. to give vanillin, carbon dioxide and isobutene. Pyrolysis/GC/MS analysis indicated that the pyrolysis was quantitative, and that the effective pyrolysis release temperature was about 175° C.

When the Example I compound was applied to cigarette paper (300 ppm) and the cigarettes were smoked, the side stream smoke had a pleasant aroma as compared to the control cigarettes. Cigarette paper treated with the Example I compound does not develop any yellow coloration under varied conditions of light and moisture.

What is claimed is:

1. A smoking composition comprising an admixture of
  (1) combustible filler selected from natural tobacco, reconstituted tobacco and tobacco substitutes, and
  (2) between about 0.0001–5 weight percent, based on the total weight of filler, of a flavorant-release additive corresponding to the formula:

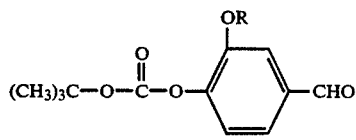

where R is methyl or ethyl.

2. A smoking composition is accordance with claim 1 wherein the flavorant-release additive is 4-t-butoxycarbonyloxy-3-methoxybenzaldehyde.

3. A smoking composition is accordance with claim 1 wherein the flavorant-release additive is 4-t-butoxycarbonyloxy-3-ethoxybenzaldehyde.

4. A cigarette smoking product comprising
(1) a combustible filler selected from natural tobacco, reconstituted tobacco and tobacco substitutes, and
(2) a paper wrapper which has incorporated therein a flavorant-release additive corresponding to the formula:

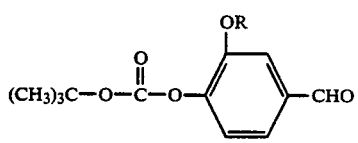

where R is methyl or ethyl.

5. A cigarette smoking product in accordance with claim 4 wherein the paper wrapper contains between about 0.01-5 weight percent of flavorant-release additive.

6. A cigarette smoking product in accordance with claim 4 wherein the flavorant-release additive in the paper wrapper is 4-t-butoxycarbonyloxy-3-methoxybenzaldehyde.

7. A cigarette smoking product in accordance with claim 4 wherein the flavorant-release additive in the paper wrapper is 4-t-butoxycarbonyloxy-3-ethoxybenzaldehyde.

8. A cigarette smoking product in accordance with claim 4 wherein the combustible filler contains between about 0.0001-5 weight percent, based on the weight of filler, of a flavorant-release additive corresponding to the formula:

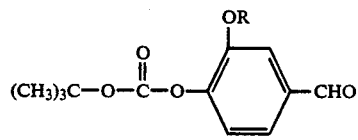

where R is methyl or ethyl.

9. A cigarette smoking product in accordance with claim 8 wherein the flavorant-release additive in the combustible filler is 4-t-butoxycarbonyloxy-3-methoxybenzaldehyde.

10. A cigarette smoking product in accordance with claim 8 wherein the flavorant-release additive in the combustible filler is 4-t-butoxycarbonyloxy-3-ethoxybenzaldehyde.

11. 4-t-Butoxycarbonyloxy-3-methoxybenzaldehyde.

12. 4-t-Butoxycarbonyloxy-3-ethoxybenzaldehyde.

* * * * *